United States Patent
Burke et al.

[11] Patent Number: 6,126,923
[45] Date of Patent: Oct. 3, 2000

[54] MAGICALLY APPEARING STRIPED DENTIFRICE

[75] Inventors: Michael R. Burke, Hale Altrincham, United Kingdom; Veerle De Bondt, Profondeville; Jean-Paul Delvenne, Seraing, both of Belgium; Tessa Plen, London, United Kingdom; Gary Tambs, Belle Mead, N.J.; Benjamin Y. Mandanas, Freehold, N.J.; Prakasarao Mandadi, Somerset, N.J.; Mike Wong, North Brunswick, N.J.

[73] Assignee: Colgate-Palmolive Company

[21] Appl. No.: 09/209,543

[22] Filed: Dec. 11, 1998

[51] Int. Cl.[7] .............. A61K 7/16; B29C 47/04; B29C 47/06; B29C 47/22

[52] U.S. Cl. ............. 424/49; 206/45.31; 206/45.34; 206/277; 222/23; 222/106

[58] Field of Search ............. 206/45.31, 45.34; 222/23, 106; 424/49–58

[56] References Cited

U.S. PATENT DOCUMENTS

| | | | |
|---|---|---|---|
| 3,980,767 | 9/1976 | Chown et al. | 424/41 |
| 4,456,585 | 6/1984 | Hayes et al. | 424/49 |
| 4,518,578 | 5/1985 | Hayes et al. | 424/49 |
| 4,585,147 | 4/1986 | Wodnicki | 222/50 |
| 5,035,347 | 7/1991 | Trovo | 222/95 |
| 5,035,349 | 7/1991 | Donahue | 222/107 |
| 5,088,623 | 2/1992 | Crawford | 222/40 |
| 5,137,178 | 8/1992 | Stokes et al. | 222/96 |
| 5,152,427 | 10/1992 | Pope et al. | 222/23 |
| 5,324,505 | 6/1994 | Kurnettka et al. | 424/49 |
| 5,328,056 | 7/1994 | Schneider et al. | 222/94 |
| 5,636,933 | 6/1997 | Vizsolyi | 401/269 |

FOREIGN PATENT DOCUMENTS

| | | |
|---|---|---|
| 00 76 563 | 4/1983 | European Pat. Off. |
| 0585846 | 3/1984 | European Pat. Off. |
| 0 333 956 | 9/1989 | European Pat. Off. |
| 0 491 093 | 6/1992 | European Pat. Off. |
| 0 661 041 | 7/1995 | European Pat. Off. |
| 1 289 323 | 9/1972 | United Kingdom . |
| 1 342 755 | 1/1974 | United Kingdom . |
| 98/ 51580 | 11/1998 | WIPO . |

Primary Examiner—Shep K. Rose
Attorney, Agent, or Firm—Paul Shapiro

[57] ABSTRACT

A method for forming a striped dentifrice wherein a first dentifrice which appears unstriped when stored in a container having sidewalls at least a portion of which is transparent, is transformed into a striped dentifrice upon extrusion from the container, which method comprises storing the first dentifrice in the container provided with discharge means and striping means within the discharge means, sequentially filling the container with a striping dentifrice having a color which distinguishes the striping dentifrice from the first dentifrice, the striping dentifrice being stored in an area of the container separate from the first dentifrice, followed by filling the container with the first dentifrice, applying pressure on the dentifrices to cause the striping dentifrice to be applied to the first dentifrice within the container area in which the second dentifrice is stored and be simultaneously extruded together from the container, so that upon extrusion, the extruded dentifrice appears to have been magically transformed into a striped body.

5 Claims, 1 Drawing Sheet

MAGICALLY APPEARING STRIPED DENTIFRICE

BACKGROUND OF THE INVENTION

1. Field of the Invention

This invention relates to a striped dentifrice product and more particularly to a striped toothpaste or gel stored in a container wherein at least a portion of the sidewalls are transparent or translucent so that when viewed by the consumer through the sidewalls the dentifrice is unstriped but when dispensed, the dentifrice is surface striped, as if by magic, by a second dentifrice having a distinguishable color.

2. The Prior Art

Aesthetic effects have been acknowledged to play an important role in consumer acceptance of many products. In many cases ornamental effects have been used to distinguish particular products in the marketplace and identify products having particular distinct properties. In the dentifrice field, toothpastes and gels which have incorporated therein contrasting colored stripes are known. Such stripes provide an aesthetic effect which the consumer finds pleasing and promotes the use of the dentifrice, particularly by children. Although such products have met with consumer approval, it has been found desirable to market a dentifrice having a first color packaged and stored in a collapsible container having at least a transparent portion through which the dentifrice product stored within the container may be viewed wherein the striped effect of a second dentifrice of a different color appears magically upon the surface of the stored dentifrice as it is dispensed from the container.

SUMMARY OF THE INVENTION

In accordance with the present invention there is provided an aesthetically pleasing striped dentifrice. The stripe is created when there is dispensed from a container a first unstriped dentifrice which is contacted under pressure with a second dentifrice having a color distinguishable from the first, the second dentifrice being maintained in the container separately from the first dentifrice, the container having sidewalls at least a portion of which are transparent, through which the unstriped first dentifrice can be viewed by the user whereby the second dentifrice is deposited as a surface stripe on the first dentifrice when activated under pressure, the two dentifrices being simultaneously extruded from the container. The extrusion, as viewed by the user, magically creates a distinct striped effect on the second dentifrice, the color of the stripes being distinguishable from the first dentifrice.

The container used in the present invention before pressure is applied thereto appears to the consumer as containing an unstriped dentifrice. When pressure is applied to the container contents, there is unexpectedly extruded from the container, as if by magic, a striped ribbon of dentifrice which is presented to the consumer in a very appealing form. Dentifrice which is magically transformed from an unstriped to a striped form is a particularly appealing form of the product thereby promoting use of the product by consumers, especially children.

DESCRIPTION OF THE PREFERRED EMBODIMENTS

The term "transparent" as used herein means having the property of being visible and includes within its meaning bodies which are translucent as well as being visually clear.

The term "different color" includes within its meaning a color which is distinguishable from a first color either by shade, which is lighter or darker than the first color or is dissimilar or contrasting to the first color.

The compositions of the first and second dentifrices with which the transparent container of the present invention is filled are of substantially the same composition except for the fact that the dentifrices contain different colorants abrasive and thickener contents. It is within the scope of the present invention that the first dentifrice may not contain any colorant and may be translucent or visually clear. The colorants used to prepare the individual dentifrice components are pharmacologically and physiologically non-toxic when used in the suggested amounts. The colorants include both pigments an dyes. Pigments useful in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns. Dentifrices which contain pigments are referred to herein as "pastes".

Dyes used in the practice of the present invention are distributed uniformly throughout the dentifrice and are desirably food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-Æ-3,5-cyclohexadienimine], FD&C Blue No. 1 (disodium salt of dibenzyldiethyl-diaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the dentifrice in an amount from about 0.05 percent to about 10 percent by weight with respect to the weight of the total composition and preferably present from about 0.1 percent to about 5 percent of the total weight of the composition. Dentifrices which contain dye colorants are referred to herein as "gels".

In the practice of the present invention it is preferred that when a colorant included in the first or base dentifrice packaged in the transparent container be a lake dye or pigment and that colorant included in the second striping dentifrice be a food color dye.

In the preparation of the first and second dentifrice components in accordance with the present invention there is utilized an orally acceptable vehicle, including a water-phase with humectant which is preferably glycerine or sorbitol or an alkylene glycol such as polyethylene glycol or propylene glycol, wherein the water is present typically in amount of about 5 to about 25% by weight and the glycerine, sorbitol and/or the alkylene glycol ingredients typically total about 20 to about 60% by weight of the dentifrice, more typically about 25 to about 50% by weight.

Both dentifrice components typically contain a natural or synthetic thickener or gelling agent in proportions of about 0.0 to about 5% by weight, preferably about 0.2 to about 1% by weight. These proportions of thickeners in the dentifrice compositions of the present invention are sufficient to form an extrudable, shape-retaining product which can be squeezed from a tube onto a toothbrush and will not fall between the bristles of the brush but rather, will substantially maintain its shape thereon. Suitable thickeners or gelling agents useful in the practice of the present invention include Irish moss, iota-carrageenan, gum tragacanth, starch, polyvinylpyrrolidone, hydroxyethylpropyl-cellulose, hydroxybutyl methyl cellulose, hydroxypropyl methyl cellulose, hydroxyethyl cellulose and carboxymethyl cellulose.

Polishing agents such as silica, calcined alumina, sodium bicarbonate, calcium carbonate, dicalcium phosphate and calcium pyrophosphate may be included in the dentifrice compositions used in the practice of the present invention. Visually clear dentifrice compositions are obtained by using polishing agents such as collodial silica, such as those sold under the trademark Toxosil 103 or alkali metal aluminosilicate complexes (that is, silica containing alumina combined in its matrix) which have refractive indices close to the refractive indices of gelling agent-liquid (including water and/or humectant) systems used in dentifrice compositions.

The polishing material is generally present in the gel or paste compositions in weight concentrations of about 3% to about 50% by weight.

Surfactants are used in the dentifrice compositions of the present invention to achieve increased prophylactic action and render the instant compositions more cosmetically acceptable. Suitable examples of surfactants include water-soluble salts of higher fatty acid monoglyceride monosulfates, such as the sodium salt of the monsulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

The anionic surfactants are typically present in the dentifrice compositions of the present invention in an amount of about 0.3 to about 5% by weight, preferably about 0.5 to about 2.0% by weight.

The dentifrice compositions of the present invention may also contain a source of fluoride ions as anticaries agent in amount sufficient to supply about 25 ppm to 2500 ppm of fluoride ions and include inorganic fluoride salts, such as soluble alkali metal salts, for example, sodium fluoride, potassium fluoride, sodium monofluorophosphate and mixtures thereof.

Typically, in the case of alkali metal fluorides, these salts are present in an amount up to about 2% by weight, based on the weight of the preparation, and preferably in the amount of about 0.05% to 1%.

In addition to fluoride compounds, there may also be included anticalculus agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimetaphosphate which are included in the dentifrice composition at a concentration of about 1 to 5% by weight.

Sweeteners well known to the art, including natural and artificial sweeteners, may be used. The sweetener may be selected from a wide range of materials including naturally occurring water-soluble sweeteners and artificial water-soluble sweeteners. Artificial water-soluble sweeteners include but are not limited to, soluble saccharin salts, e.g., sodium or calcium saccharin salts and cyclamate salts. Naturally occurring water-soluble sweeteners include, but are not limited to sucrose, sugar alcohols, including sorbitol as 70% sorbitol solution, mannitol, xylitol, maltitol, hydrogenated starch hydrolysates and mixtures thereof. The sweetener is present in the dentifrice at a concentration of about 0.1 to about 5% by weight.

The dentifrice compositions of the present invention may contain a flavoring agent. The flavoring agent is incorporated in the dentifrice composition of the present invention at a concentration of about 0.1 to about 5.0% by weight and preferably about 0.5 to about 1.5% by weight. Flavoring agents which are used in the practice of the present invention include essential oils as well as various flavoring aldehydes, esters, alcohols and similar materials. Examples of the essential oils include oils of spearmint, peppermint, wintergreen, sassafras, clove, sage, eucalyptus, marjoram, cinnamon, lemon, lime, grapefruit and orange. Also useful are such chemicals as menthol, carvone and anethole. Of these, the most commonly employed are the oils of peppermint and spearmint.

Various other materials may be incorporated in the oral preparations of this invention such as antibacterial agents such as triclosan, chlorhexidiene, anionic polymeric carboxylates such as methyl vinyl etherl/maleic anhydride copolymers, desensitizers such as potassium nitrate, vitamins such as panthenol, retinyl palmitate, tocopherol acetate, herbs such as chamomilla recutita, mentha piperita, salvia officinalis, commiphora myrrha, whitening agents such as hydrogen peroxide and urea peroxide, preservatives, silicones, chlorophyll compounds and/or ammoniated materials such as urea, diammonium phosphate, and mixtures thereof. These adjuvants, when present, are incorporated in the dentifrice composition in amounts which do not substantially adversely affect the properties and characteristics desired.

The two dentifrice components of the present invention may be simultaneously dispensed in controlled quantities from a container, such as a pressurized container, pump or collapsible tube by applying pressure on the components which pressure is activated by the user. Containers suitable for such dispensing are known to the art, as for example, as disclosed in U.S. Pat. Nos. 4,687,663 and 4,487,663, the disclosures of which are incorporated herein by reference.

IN THE DRAWINGS

Figure 1:
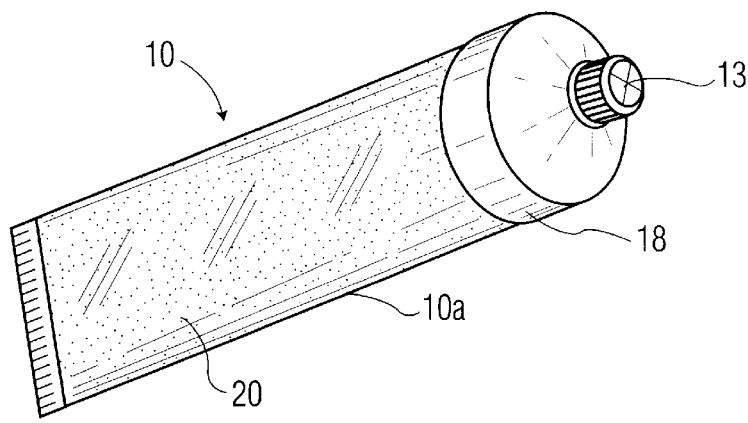
FIG. 1 is a an elevational view of one embodiment of the present invention in which is shown a collapsible tube having transparent sidewalls for dispensing the dual dentifrice components stored therein simultaneously in striped form.
Figure 2:
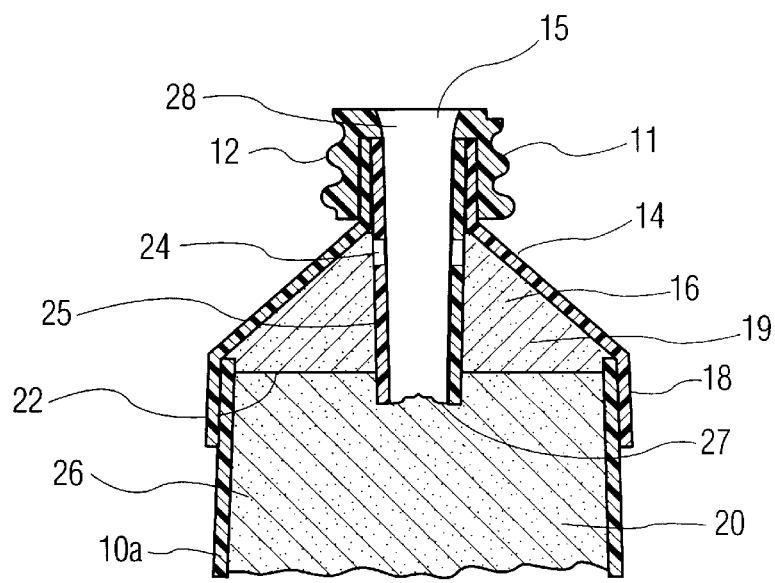
FIG. 2 is a partial central sectional view of the collapsible tube containing the two dentifrice components to be dispensed simultaneously in striped form.
Figure 3:
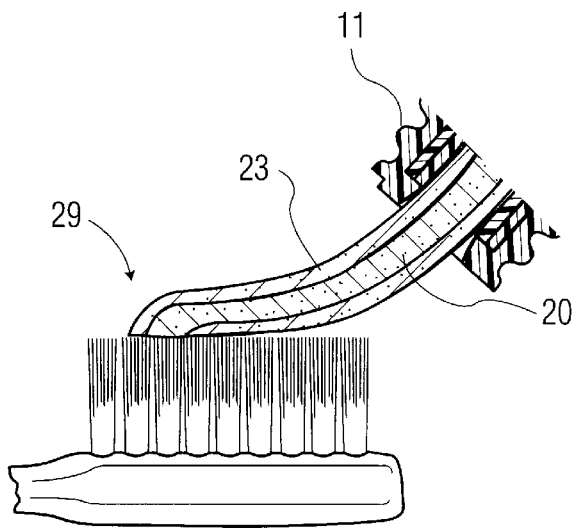
FIG. 3 is a sectional view of a portion of the collapsible tube in which the two portions of the dentifrice are extruded together as an attractive striped product.

Referring now to the embodiment of the invention as illustrated in FIGS. 1 to 3 of the drawings, a collapsible dispensing tube 10 having transparent sidewalls 10a is provided with a threaded head end 11 having a plurality of threads 12 for securing a cap 13 to the head of end of the tube 10 having a sloping forward end 14 and a discharge passageway or port 15.

The tube 10 is formed from a plastic material such as high density polyethylene or polypropylene having sufficiently thin sidewalls as to be capable of being repeatedly flexed to apply pressure to dispense the dentifrice components stored in the tube.

Positioned within the sloping forward end 14 of the tube 10 is a zone under the head end which extends from the threaded head end 11 back into the tube 10 to define first zone 16 which is concealed from view by the opaque skirt 18 of the sloping forward end 14.

The first zone 16 which is enclosed by the sloping forward end 14 and hidden from view by the opaque skirt 18 of the tube 10 is filled with striping gel 19 having a first color. The balance of the tube 10 is filled with a paste 20 of contrasting color and forms the body of the toothpaste to be striped upon compression of the sidewalls 10a of the tube 10, the gel 19 and paste 20 contacting each other in zone 16 along surfaces 22.

In order for the striping gel 19 contained within the zone 16 to be placed as stripes 23 on the extruded ribbon body of the paste 20, at least one and preferably a plurality of striping passages 24 is formed within the insert 25 positioned within the discharge passageway 15 of the head end 11, the insert 25 communicating between the discharge passageway 15 and the second zone 26 of the tube 10 where the paste 20 is stored. In order to produce a colored stripe of a particular width, the width of the striping port 24 must be no wider than the stripe produced. Slight spreading of this stripe may occur as the paste 20 leaves the tube port 15, the extent depending on such factors as, for example, paste viscosity and extrusion pressure. However, for good reproducibility and sharpness of stripe, only slight spreading is permissible. Therefore, the width of the striping port 24 must be the same as or slightly less then the width of the stripe 23 to be produced.

In operation, the tube 10 is filled with the dentifrice components to be dispensed in the form of a striped ribbon 29 by first charging into the tube 10, the dentifrice gel 19 which is to form the stripes. This material is charged into first zone 16 in a quantity such that it does not fill the container beyond the inlet 27 of the insert 24 and above the point 22 where the two different colored dentifrice materials will be in contact within the tube 10. The paste material which is to form the body 20 of the extruded striped ribbon 29 is then charged into the tube 10 to fill the balance of the tube space at least a portion which is visible to the user through the transparent sidewalls 10a. The volume ratio of striping gel 19 to base dentifrice paste 20 is generally in the range of 1:6 to 1:15 and preferably 1:9.

When pressure is applied to the sidewalls 10a of tube 10 to dispense the striped dentifrice ribbon 29, the paste 20 which forms the body of the striped dentifrice 29 is extruded out through the inlet 27 of the insert 25 leading to the discharge port 15 of the tube 10 through discharge passageway 12. At the same time, the pressure applied to the sidewalls 10a of the tube and thereby to the paste material 20 is also transmitted by the paste 20 longitudinally in a forward direction to the striping gel 19 packed in the zone 16 of the tube 10. As a consequence of this pressure, the striping gel 19 is forced through the striping port 24 onto the ribbon of paste material 20 passing through the discharge passageway 28 of the insert 25. In this manner, the striping gel 19 is made part of the paste ribbon 29, and both dentifrices emerge from the discharge port 15 of the tube 10 in the form of a striped ribbon 29 which appears to form magically as the unstriped paste viewed through the transparent sidewalls 10a of the tube 10 is dispensed.

The present invention is illustrated in terms of its preferred embodiments in the accompanying Example. All parts and percentages referred to in this specification and the appended claims are by weight example.

EXAMPLE

|  | Gel (Wt. %) | Paste (Wt. %) |
| --- | --- | --- |
| Water | 8.85 | 8.35 |
| Glycerin | 10.0 | 10.0 |
| Carboxymethylcellulose | 0.40 | 0.40 |
| Saccharin | 0.30 | 0.30 |
| Polyethylene glycol 600 | 3.0 | 3.0 |
| Sorbitol | 52.2 | 52.2 |
| Sodium fluoride | 0.32 | 0.32 |
| Toxosil 103 | 18.0 | 18.0 |
| Zeodent 165 | 4.5 | 4.5 |
| Sodium lauryl sulfate | 1.5 | 1.5 |
| Color (1% blue dye solution) | 0.95 | 0.95 |
| Titanium dioxide | — | 0.50 |

In the preparation of the gel and paste compositions a vehicle solution of the glycerine, sorbitol, polyethylene glycol 600 and water was made and subjected to 28–30 lbs applied vacuum and a mixture of saccharin sodium fluoride and carboxymethylcellulose was added thereto. Subsequently, the dye or $TiO_2$ was blended with the vehicle. The mixture was degassed at 28–30 lbs applied vacuum over a 5 minute period. Then, the Toxosil 103, Zeodent 165 and sodium lauryl sulfate were added after preliminary degassing. The ingredients were mixed. After about 5 minutes mixing, with application of vacuum, the dentifrice preparation was considered to be complete and the gel and paste components were packed into tubes of the type illustrated in the FIGS. 1–2 of the drawing at a volume ratio of 1:9. Only the paste was viewable in the tube 10, the gel component being hidden from view by the opaque skirt 14 affixed to the top end of the tube.

After packaging, the dentifrice product was squeezed from a tube and was extruded as a distinctive striped ribbon product of continuous blue stripes extending the length of surface of the white dentifrice product which stripes appeared spontaneously as if by magic on the white toothpaste being extruded.

What is claimed is:

1. A method for extruding a striped dentifrice wherein a first dentifrice which appears unstriped when stored in a container having sidewalls at least a portion of which is transparent, is transformed into a striped dentifrice upon extrusion from the container, the container having discharge means and striping means within the discharge means, which method comprises storing the first dentifrice in the container portion which is transparent and in which the first dentifrice is visible to the user, sequentially filling the container with a striping dentifrice having a color which distinguishes the striping dentifrice from the first dentifrice, the striping dentifrice being stored in an area of the container concealed from view by the user of the container, followed by filling the container with the first dentifrice, applying pressure on the dentifrices to cause the striping dentifrice to be applied to the first dentifrice within the container area in which the second dentifrice is stored and be simultaneously extruded together from the container, so that upon extrusion, the extruded dentifrice appears to have been magically transformed into a striped body.

2. The method of claim 1 wherein the container is filled with the striping dentifrice and first dentifrice at a volume ratio of about 1:6 to 1:15.

3. The method of claim 1 wherein the first dentifrice contains pigment.

4. The method of claim 1 wherein the striping dentifrice contains a dye.

5. The method of claim 3 wherein the pigment is titanium dioxide.

* * * * *